United States Patent
Patel et al.

(10) Patent No.: US 9,332,896 B2
(45) Date of Patent: May 10, 2016

(54) LARYNGOSCOPE

(75) Inventors: Anil Patel, Cheam (GB); Peter Young, Kings Lynn (GB); Marko Plevnik, London (GB)

(73) Assignee: Indian Ocean Medical Inc., Mahe (SC)

( * ) Notice: Subject to any disclaimer, the term of this patent is extended or adjusted under 35 U.S.C. 154(b) by 0 days.

(21) Appl. No.: 13/392,627

(22) PCT Filed: Aug. 12, 2010

(86) PCT No.: PCT/GB2010/001535
§ 371 (c)(1),
(2), (4) Date: Apr. 11, 2012

(87) PCT Pub. No.: WO2011/023930
PCT Pub. Date: Mar. 3, 2011

(65) Prior Publication Data
US 2012/0190929 A1    Jul. 26, 2012

(30) Foreign Application Priority Data

Aug. 28, 2009  (GB) .................................. 0915107.7

(51) Int. Cl.
*A61B 1/32*  (2006.01)
*A61B 1/05*  (2006.01)
(Continued)

(52) U.S. Cl.
CPC ................ *A61B 1/05* (2013.01); *A61B 1/00096* (2013.01); *A61B 1/00183* (2013.01); *A61B 1/045* (2013.01); *A61B 1/267* (2013.01)

(58) Field of Classification Search
CPC ........... A61B 17/0218; A61B 17/3423; A61B 17/02; A61B 17/0293
USPC ................................................. 600/184–200
See application file for complete search history.

(56) References Cited

U.S. PATENT DOCUMENTS 3,426,749 A    2/1969  Jephcott
4,337,761 A *  7/1982  Upsher ......................... 600/188

(Continued)

FOREIGN PATENT DOCUMENTS

CN    2870731 Y    1/2006
CN    2770570 Y    4/2006

(Continued)

OTHER PUBLICATIONS

Patent Examination Report No. 1 in Australian patent application No. 2010288342, dated Aug. 22, 2013.

(Continued)

*Primary Examiner* — Mary Hoffman
(74) *Attorney, Agent, or Firm* — Ostrager Chong Flaterty & Broitman P.C.

(57) ABSTRACT

A laryngoscope comprising a handle, a blade holding element, a detachable blade, means for viewing the laryngeal inlet of a patient and means for adjusting the viewing field. The means for adjusting the viewing field may comprise a light refracting means. Alternatively, in embodiments in which the viewing means comprises at least two fixed cameras elements directed to at least two different viewing fields, the means for adjusting the viewing field may comprise means for switching from one camera to the other or, in embodiments in which the viewing means comprises a movable camera element, the means for adjusting the viewing field may comprise mechanical or electronic means for controlling the movement of the camera. A method for viewing the laryngeal inlet of a patient using a laryngoscope comprising the step of adjusting the viewing field is also covered.

35 Claims, 21 Drawing Sheets

(51) Int. Cl.
*A61B 1/00* (2006.01)
*A61B 1/045* (2006.01)
*A61B 1/267* (2006.01)

(56) References Cited

U.S. PATENT DOCUMENTS

| | | | |
|---|---|---|---|
| 4,574,784 A | 3/1986 | Soloway | |
| 4,579,108 A | 4/1986 | Bauman | |
| 4,834,077 A | 5/1989 | Sun | |
| 5,261,392 A | 11/1993 | Wu | |
| 5,347,995 A | 9/1994 | Slater et al. | |
| 5,349,943 A * | 9/1994 | Ruiz | 600/189 |
| 5,381,787 A | 1/1995 | Bullard | |
| 2003/0168059 A1 | 9/2003 | Pacey | |
| 2003/0181789 A1 | 9/2003 | Mazzei | |
| 2004/0220454 A1 | 11/2004 | Dalle et al. | |
| 2005/0240081 A1 | 10/2005 | Eliachar | |
| 2007/0175482 A1 * | 8/2007 | Kimmel et al. | 128/207.14 |
| 2007/0287888 A1 | 12/2007 | Lovell | |
| 2008/0064926 A1 | 3/2008 | Chen | |
| 2008/0208006 A1 * | 8/2008 | Farr | 600/178 |
| 2009/0099421 A1 | 4/2009 | Shalman et al. | |
| 2009/0299146 A1 * | 12/2009 | McGrath | 600/188 |
| 2010/0041955 A1 * | 2/2010 | Grey et al. | 600/212 |
| 2010/0081875 A1 * | 4/2010 | Fowler et al. | 600/114 |
| 2010/0198009 A1 * | 8/2010 | Farr et al. | 600/109 |
| 2011/0028790 A1 * | 2/2011 | Farr et al. | 600/187 |

FOREIGN PATENT DOCUMENTS

| | | |
|---|---|---|
| CN | 101360446 A | 2/2009 |
| CN | 201194790 Y | 2/2009 |
| EP | 1166710 A2 | 1/2001 |
| EP | 1598001 A1 | 11/2005 |
| EP | 1640033 A1 | 3/2006 |
| FR | 2381528 A1 | 9/1978 |
| JP | 19935501967 A | 4/1994 |
| JP | 200824221 | 1/1996 |
| JP | H08112252 | 5/1996 |
| JP | H11123175 | 11/1998 |
| JP | 2000184607 | 1/2002 |
| JP | 2002000732 | 1/2002 |
| JP | 200265589 A | 3/2002 |
| JP | 2005520586 | 7/2005 |
| JP | 2006525058 A | 11/2006 |
| JP | 2006326111 | 12/2006 |
| JP | 2006326111 A | 12/2006 |
| JP | 2007117116 A | 5/2007 |
| JP | 2008119305 A | 5/2008 |
| JP | 200853551 | 9/2008 |
| JP | 2008535551 A | 9/2008 |
| JP | 2008289669 A | 12/2008 |
| JP | 2009531133 | 9/2009 |
| TW | 201021755 A1 | 6/2010 |
| WO | 9014041 | 11/1990 |
| WO | 0030707 A2 | 6/2000 |
| WO | 2006102770 A1 | 10/2006 |
| WO | 2007066134 A2 | 6/2007 |
| WO | 2007126657 A1 | 11/2007 |
| WO | 2008157170 A2 | 12/2008 |
| WO | 2009027669 A2 | 3/2009 |
| WO | 2010049694 A1 | 5/2010 |

OTHER PUBLICATIONS

First Office Action in China Patent Application No. 201080043321X.
Notice of Reasons for Rejection in Japanese Patent Application No. 2012-526108, dated Oct. 25, 2013.
Patent Examination Report No. 1 in Application No. 2009309483, Applicant: Indian Ocean Medical Inc., IP Australia, Oct. 3, 2013.
Notification of Reason for Refusal in Japanese Patent Application No. 2011-533817, Japanese Patent Office, Jun. 18, 2013.
Notification of Reason for Refusal in Japanese Patent Application No. 2012-505216, Japanese Patent Office, Aug. 14, 2013.
3rd Notification of Office Action from State Intellectual Property Office of China in Application No. 200980143038.1, Applicant: Indian Ocean Medical Inc., Jul. 15, 2014.
Patent Examination Report No. 2 in Application No. 2010288342, Applicant: Indian Ocean Medical Inc., IP Australia, Oct. 22, 2014.
2nd Notification of Office Action from State Intellectual Property Office of China in Application No. 201080043321.X, Applicant: Indian Ocean Medical Inc., Nov. 19, 2014.
Notice of Reasons for Rejection in Japanese Patent Application No. 2014-230569, mailed Oct. 19, 2015.
Office Action dated Jan. 26, 2016 in corresponding Taiwan patent application No. 099127262.

* cited by examiner

LARYNGOSCOPE

FIELD OF THE INVENTION

This application relates to a laryngoscope and more particularly to a video laryngoscope.

BACKGROUND OF THE INVENTION

Whereas a conventional laryngoscope is used by a physician to visualise the path to the trachea by manipulating the patient's anatomy to establish a direct line of sight, a video laryngoscope provides a view of the glottis and trachea without the need for such manipulation, which is clearly advantageous.

In recent times video laryngoscopes have also been provided that have removable, disposable blades, to remove the need for sterilisation.

A laryngoscope is a device which is used by clinicians during tracheal intubation and that assists with intubation by allowing the clinician to visualise the path of the endotracheal tube as it passes through the glottis towards the trachea. In its most recent form a laryngoscope comprises a handle and a blade and often includes a light source. Some laryngoscopes are also provided with viewing devices such as fibre optics and cameras. These are called video laryngoscopes.

Most intubations are straightforward and clinicians use a laryngoscope with a straight or curved blade which is positioned into the patient's airway. However, some patients are known to be difficult to intubate, especially if there are anatomical abnormalities (e.g. if the larynx lies particularly anteriorly) or if there are injuries. Intubation of these patients is more successful using a blade with a different shape, such as the "difficult blade" described in more detail below. A blade for use in difficult intubations preferably has a curved portion that smoothly follows the anatomical shape of the patient's airways, a ventrally displaced distal extension to allow a better view of the laryngeal inlet and a paddle to guide the endotracheal tube towards the laryngeal inlet.

There is currently no universal blade that can be used in all cases and a number of different blades may be desired and beneficial so that the clinician can visualise the laryngeal inlet with a choice of blade shapes depending upon clinical requirements and personal expertise and preference. Since existing video laryngoscopes are necessarily used with one compatible blade shape, the user will need to use an entirely different laryngoscope depending on the situation. For example, a clinician could insert a video laryngoscope with a standard curved blade into a patient and upon insertion realise that abnormalities are present which require a modified blade. He or she would then need a second video laryngoscope with a modified blade to visualise the laryngeal inlet, thereby adding to the cost of the equipment required to perform efficiently. The blades are often disposable and relatively cheap, whereas the handle comprising the viewing means is generally expensive. There is therefore a need for a laryngoscope which may be used with different blade shapes.

It is an object of this invention to seek to mitigate problems such as those described above.

SUMMARY OF THE INVENTION

According to a first aspect of the invention, there is provided a laryngoscope comprising a handle, a blade holding element, a detachable blade and means for viewing the laryngeal inlet of a patient, the laryngoscope further comprising means for adjusting the viewing field. Preferably, the laryngoscope is configured to be usable with at least two different detachable blades, including for example straight blades, curved blades or blades specifically designed for difficult intubations.

The blade may comprise a sleeve portion that completely or partially surrounds the blade holding element and a distal extension which is preferably integrally moulded with the sleeve portion. Such integrally moulded blades are cheaper to produce, more robust and less prone to contamination if reused.

The detachable blade may further comprise means for guiding the endotracheal tube towards the tip of the distal extension. This is particularly useful where the clinician faces a difficult and complex intubation situation.

In a preferred embodiment, the viewing means comprises at least one fixed camera located at the distal end of the blade holding element. Preferably, means for adjusting the viewing field comprises a light refracting means, such as a prism or a wedge prism.

In another preferred embodiment, the viewing means comprises at least two fixed cameras elements directed to at least two different viewing fields. Preferably, the laryngoscope further comprises means for switching from one camera to the other so that for example the first camera is used for when the laryngoscope is fitted with a standard blade and the second camera when a difficult blade is used.

In yet another embodiment, the viewing means comprises a movable camera element. Preferably, the laryngoscope further comprises mechanical or electronic means for controlling the movement of the camera. For example, the distal end of the sleeve of the blade may comprise a window positioned such that, in use, the camera is positioned to visualise the laryngeal inlet of the patient.

According to a second aspect of the invention, there is provided a method for viewing the laryngeal inlet of a patient using a laryngoscope comprising a handle, a blade holding element, a detachable blade and means for viewing the laryngeal inlet of a patient, comprising the step of adjusting the viewing field.

BRIEF DESCRIPTION OF THE DRAWINGS

The invention will be further described with reference to the drawings, in which:

FIG. 4b shows a view obtained with the laryngoscope of FIG. 4a;

FIG. 5b shows a view obtained with the laryngoscope of FIG. 5a;

FIG. 6b shows a view obtained with the laryngoscope of FIG. 6a;

FIG. 8b shows a view obtained with the laryngoscope of FIG. 8a;

FIG. 9b shows a view obtained with the laryngoscope of FIG. 9a;

FIG. 10b shows a view obtained with the laryngoscope of FIG. 10a;

FIG. 20b shows a view obtained with the laryngoscope of FIG. 20a;

FIG. 21b shows a view obtained with the laryngoscope of FIG. 20a;

FIG. 22b shows a view obtained with the laryngoscope of FIG. 20a;

DESCRIPTION OF PREFERRED EMBODIMENTS

In this application, the terms "distal part" and "proximal part" are used relative to the medical professional, i.e. the "distal part" is used to describe the part of the device that is inserted first into the patient. The terms "dorsal" and "ventral" are used relative to the patient, i.e. the "dorsal" side is used to describe the side directed to the back of the patient and the "ventral" side is used to describe the side directed to the front of the patient.

Figure 1A:
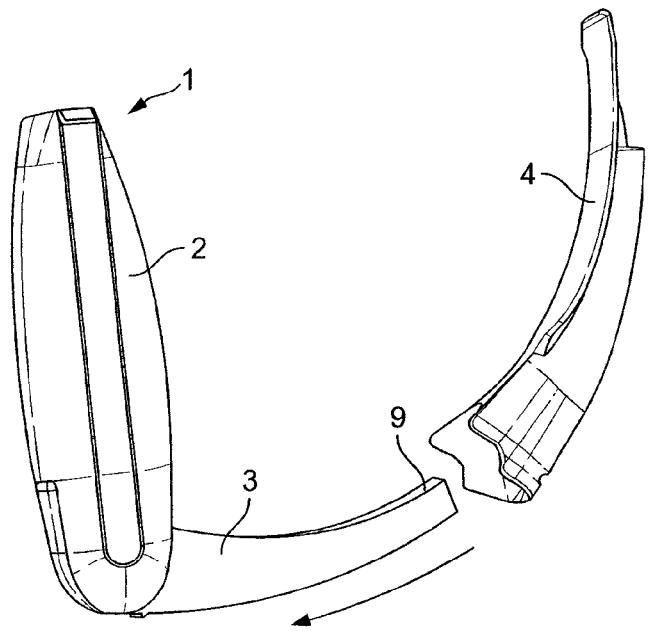
FIG. 1A to 1C show a laryngoscope according to the invention.
Figure 1B:
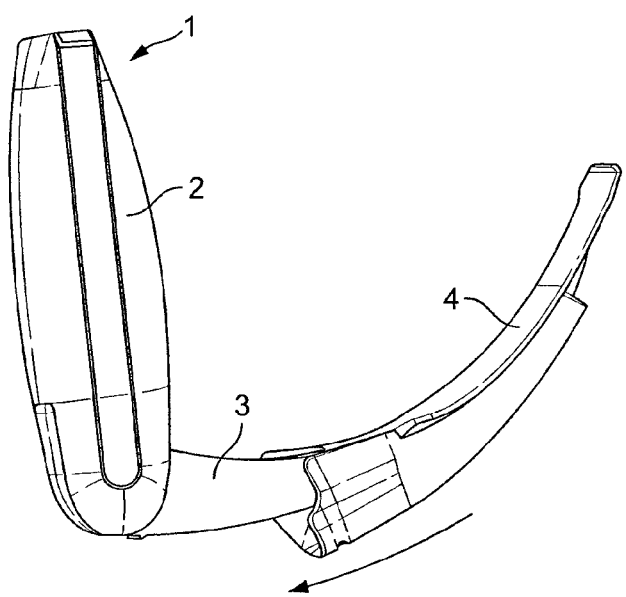
Figure 1C:
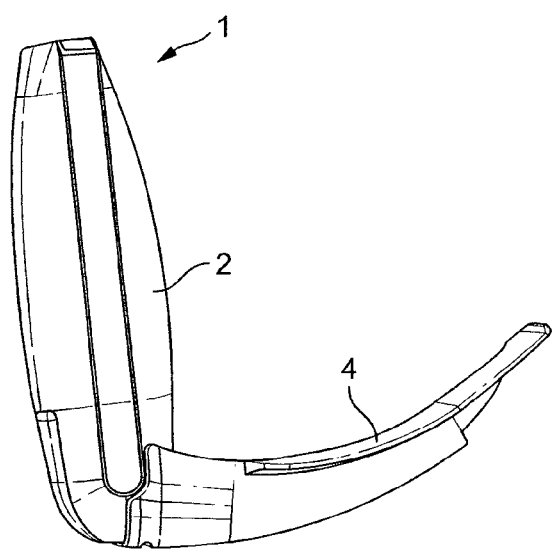

With reference to FIGS. 1A to 1C, the laryngoscope (1) comprises a handle (2) for holding and maneuvering the laryngoscope, a blade holding element (3) that is pivotally attached to the handle (2) and a detachable blade (4) that is attached the blade holding element (3).

The handle (2) is preferably made of stainless steel for robustness, although other materials such as metals or plastics may be used. At the proximal end, the blade holding element (3) is pivotally connected to the heel of the handle (2). The blade (4) is preferably hollow so that it can be fitted onto the blade holding element by sliding as can be seen in FIGS. 1A-1C (described in more detail below). Preferably, the blade holding element (3) is elongated in shape and its outer contour corresponds substantially to the inner shape of the blade (4).

The blade (4) is preferably integrally constructed and is for example produced by injection moulding so that the cost of production is relatively affordable. The blade is preferably disposable to minimise or eliminate any risk of cross-contamination between patients. The blade may be made partially or completely with a transparent material in order to view the areas surrounding the laryngeal inlet.

Figure 2A:
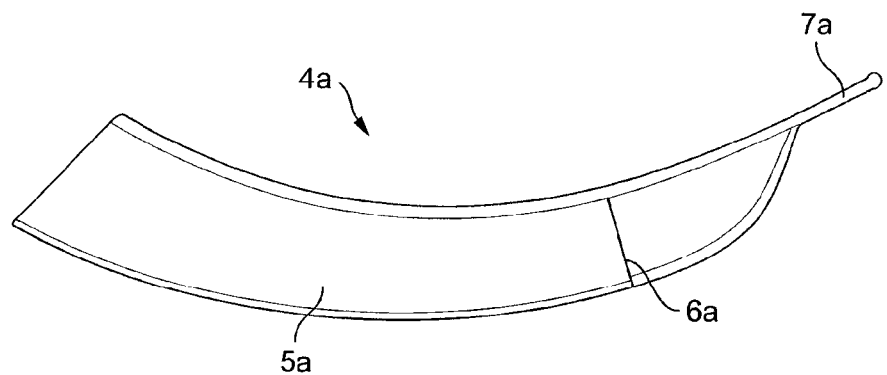
FIG. 2A shows a standard curved blade.

The blade (4) may be straight (e.g. a Miller laryngoscope blade), curved (e.g. a Macintosh blade). Curved blades are generally preferred by clinicians because they are dimensioned to conform to the anatomical curve of the patient's throat. FIG. 2A shows a standard curved Macintosh blade (4a) comprising a sleeve (5a) configured to surround, partially or completely, the blade holding element (3) and having a proximal end and a distal end. The distal end of the sleeve preferably comprises a transparent window (6a). The blade (4a) further comprises a distal extension (7a) generally following the curve of the sleeve (5a).

Figure 2B:
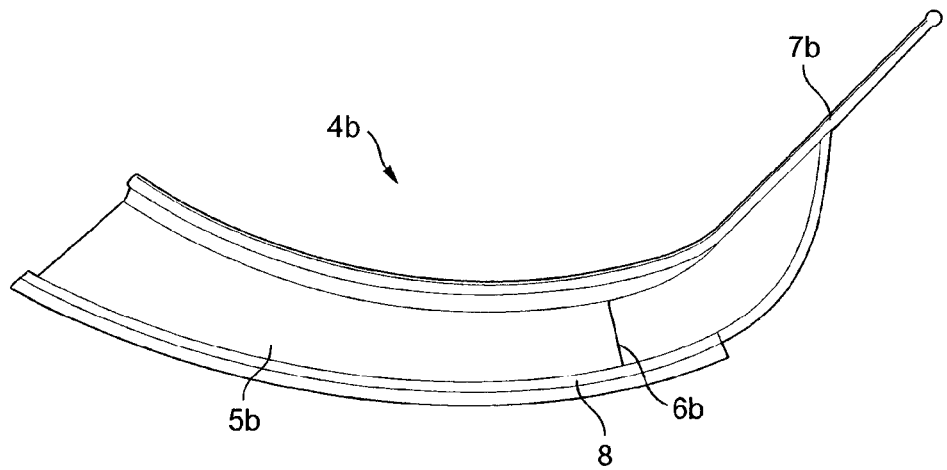
FIG. 2B shows a blade for difficult intubations.

FIG. 2B shows a blade (4b) with an enhanced longitudinal circumference. This type of blade (also referred to herein after as a "difficult blade") facilitates a view of the laryngeal inlet and is used for difficult and complex intubations.

The blade (4b) comprises a sleeve (5b) configured to surround, partially or completely, the blade holding element (3) and having a proximal end and a distal end. The distal end of the sleeve preferably comprises a transparent window (6b). The blade (4b) further comprises a distal extension (7b) is displaced ventrally from the curve of the sleeve (5b).

The difficult blade preferably comprises a guiding means for guiding the endotracheal tube into the correct position in the patient's airway. In the blade (4b) shown in FIG. 2B, the guiding device comprises a paddle extending from the distal end of the sleeve (5b) and following the curve of the sleeve to direct the tube towards the tip of the distal extension (7b).

As mentioned above, the difficult blade (4b) is recommended for difficult and complex intubations and standard Macintosh blades (4a) are used in most straightforward intubations. The standard blades (a) have the advantages of being generally cheaper than the difficult blades (4b). In addition, the difficult blades (4b) can lead to laryngeal injury when unnecessarily used for a simple straightforward intubation case. There is therefore a need for both types of blade and the clinician will choose the most appropriate blade for the situation.

The laryngoscope (1) further comprises means for viewing the laryngeal inlet of a patient. Such means can comprise a display screen (not shown) to visualise the area captured, for example, by a camera. A detachable or fixed display screen may be connected at the proximal end of the handle (2) or a separate display screen may be provided. An advantage of having a detachable screen is that the equipment can be easily cleaned after use.

Preferably, the viewing means includes at least one camera element (9) which may be located at the distal end of the blade holding element (3) so as to be directed towards the distal end of the blade (4). The image captured by the camera may be transferred to a display screen and/or other viewing means for example by means of fibre optic.

The laryngoscope (1) may also comprise a light source and/or any other visualisation means that enable external indirect visualisation of the laryngeal inlet. For example, a light source may be provided so that the distal tip of the blade is illuminated.

In operation, the laryngoscope (1) is inserted into the mouth of the patient. The blade (4) will push the tongue of the patient to the side of the oropharynx to create space through which the larynx and the epiglottis can be viewed. The blade (4) is manipulated to lift the epiglottis thereby exposing the laryngeal inlet.

An endotracheal tube can then be introduced and advanced past the vocal cords into the trachea. The endotracheal tube can be inserted together with the laryngoscope so that the tube-laryngoscope are inserted and positioned at the same time. Alternatively, the laryngoscope may be inserted first and the tube may be inserted after the laryngoscope is in the correct position. The user can visualise the distal end of the blade (4) for example on the display screen and manipulate the laryngoscope (1) accordingly. Once the tube is correctly positioned, the laryngoscope (1) is removed.

The main problem solved by the present invention is the adjustment of the viewing field so that the clinician has a clear view of the laryngeal inlet of the patient, with minimum distortion and maximum focus, regardless of the type of blade fitted onto the blade holding element. Preferably, the viewing field covers at least a 30° viewing angle below the tip of the extension (7) for optimum view of the laryngeal inlet. This area cannot be clearly viewed for example when a prior art laryngoscope configured for use with a standard blade is used with a difficult blade, because the view is obstructed by the tracheal tube guiding means and/or because of the ventral displacement of the distal extension of the blade.

Embodiment 1

Figure 3:
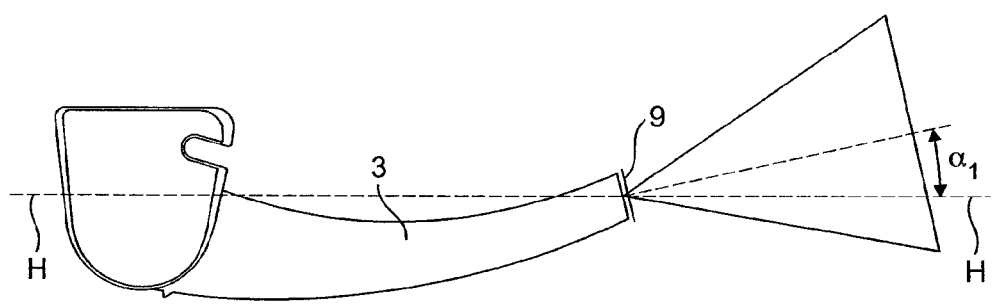
FIG. 3 shows part of a laryngoscope according to a first embodiment of the invention.

FIG. 3 shows part of a laryngoscope according to a first embodiment of the invention, in which the outer contour of the blade holding element (3) corresponds substantially to the inner shape of the sleeves (5a, 5b) of the standard and difficult blades (4a, 4b) so that the blades can be used interchangeably with the same laryngoscope. The fixed camera element (9) is located at the distal end of the blade holding element (3).

Figure 4A:
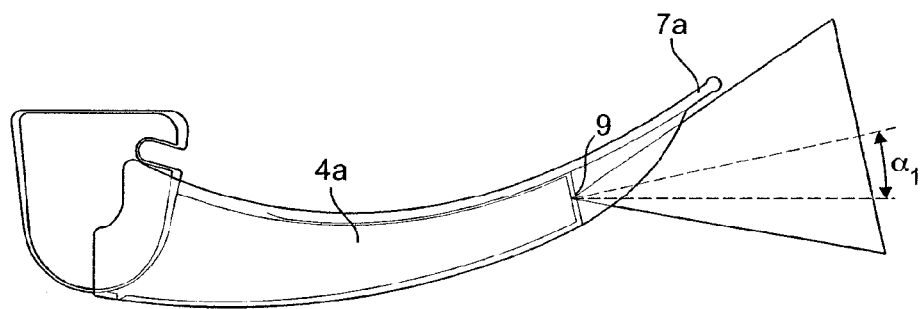
FIG. 4a shows the laryngoscope of FIG. 3 fitted with a short standard curved blade.
Figure 5A:
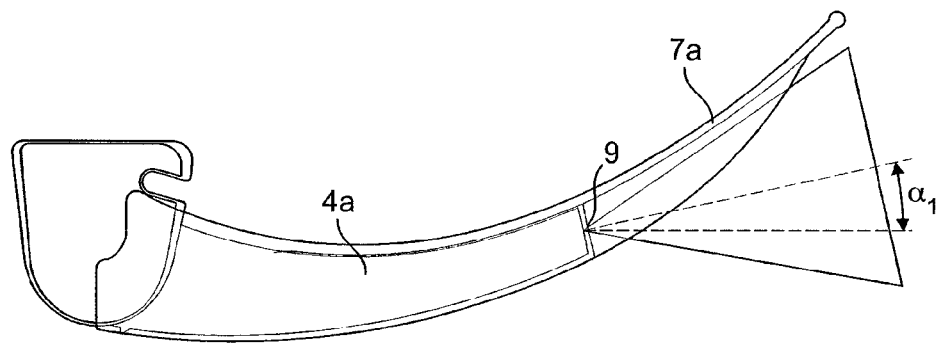
FIG. 5a shows the laryngoscope of FIG. 3 fitted with a long standard curved blade.

In FIGS. 4a and 5a, the blade holding element (3) is fitted with a short standard curved blade and with a long standard curved blade (4a), respectively. Line H-H passes between the centre of the lens of the camera (9) and the pivotal joint between the handle (2) and the blade holding element (3). The camera (9) is arranged so that the centre of the visual field captured by the camera is located at an angle $\alpha_1$ ranging for example from 5° to 15° from line H-H in the plan defined by line H-H and the longitudinal axis of the handle (2). In FIGS. 4a and 5a, the exemplary angle is 12.75° and there is minimum blade intrusion into the view frame.

Figure 4B:
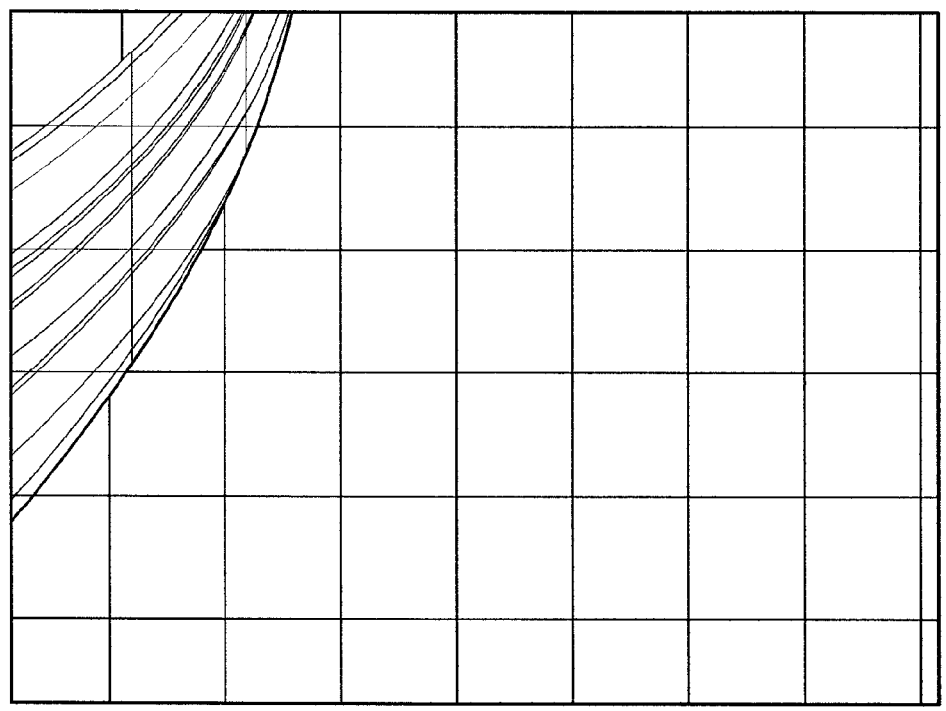
Figure 5B:
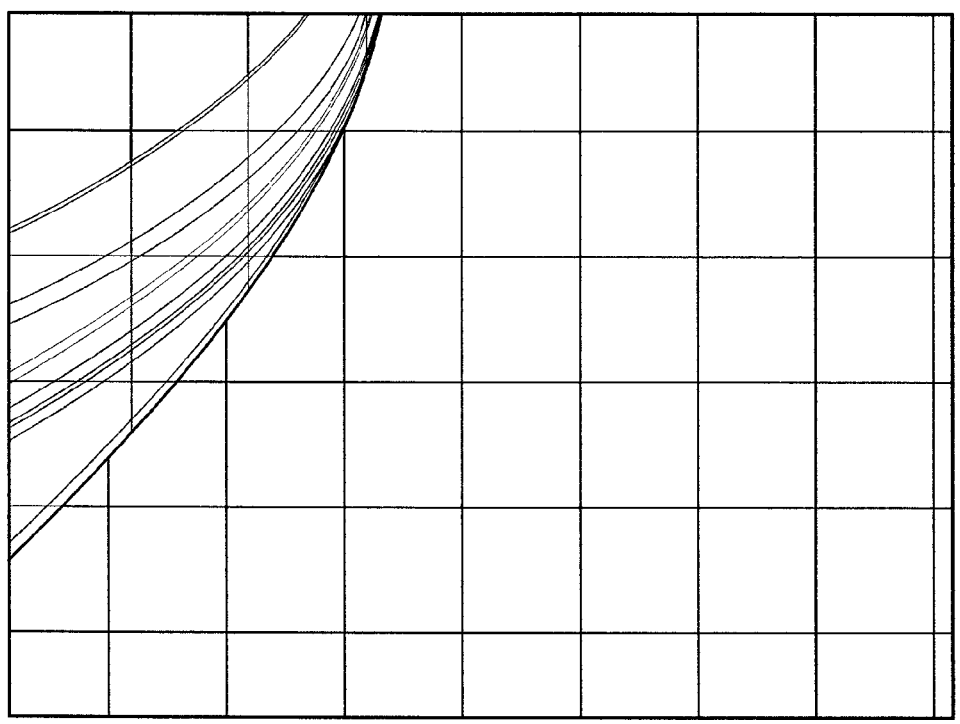

The views captured by the camera (9) are shown in FIGS. 4b and 5b. The views are clear and not distorted (as illustrated by the perfectly square grid). These are satisfactory views but ideally the tip of the distal extension (7a) should be visible so that the view is precisely focused on the laryngeal inlet of the patient.

Figure 6A:
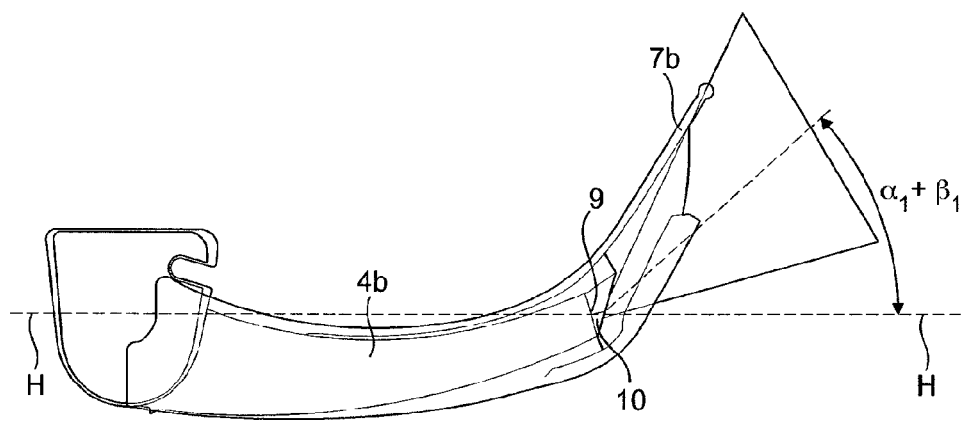
FIG. 6a shows the laryngoscope of FIG. 3 fitted with a difficult blade.
Figure 6B:
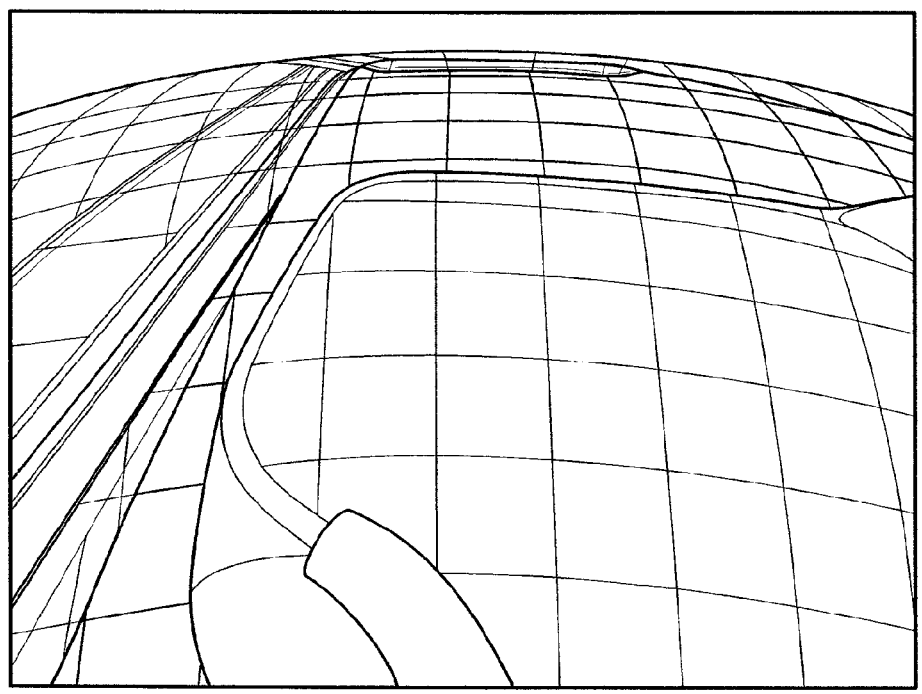

In FIG. 6a, the blade holding element (3) is fitted with a difficult blade (4b). The distal end of the sleeve (6b) comprises a wedge prism that redirects the optical pathway so that the tip of the extension (7b), and therefore the laryngeal inlet of the patient, is visible as shown in FIG. 6b. Preferably, the prism is chosen so that the centre of the visual field captured by the camera is located for example at an angle ranging from 20° to 40°. In FIG. 6b, the exemplary strength of the prism is 29° which provides an exemplary angle of 35.75° (corresponding to the original angle $\alpha_1$ of 12.75° plus a ventral tilt $\beta_1$ of 23°). However, the view captured by the camera (9) is slightly distorted as can be seen by the compressed grid lines on FIG. 6b.

In this first embodiment, the laryngoscope can be used with interchangeable blades. When fitted with a standard curved blade, no prism is required since a satisfactory view is obtained using a strategic positioning of the camera. For difficult intubations, the clinician replaces the standard curved blade with a difficult blade fitted with a prism as described above to adjust the view so that a clear, non-distorted view of the laryngeal inlet is obtained.

Embodiment 2

Figure 7:
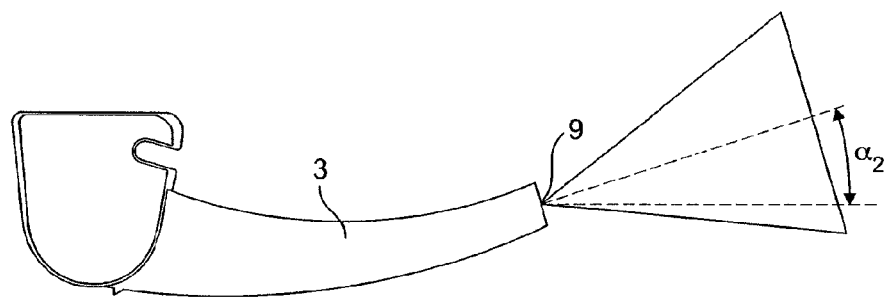
FIG. 7 shows part of a laryngoscope according to a second embodiment of the invention.

FIG. 7 shows part of a laryngoscope according to a second embodiment of the invention. The main difference with the laryngoscope of FIG. 3 lies in the position of the camera (9). The camera (9) is arranged so that the centre of the visual field captured by the camera is located at an angle $\alpha_2$ ranging for example from 15° to 25° from line H-H in the plan defined by line H-H and the longitudinal axis of the handle (2). The angle $\alpha_2$ is greater than $\alpha_1$ (for example 17°)

Figure 8A:
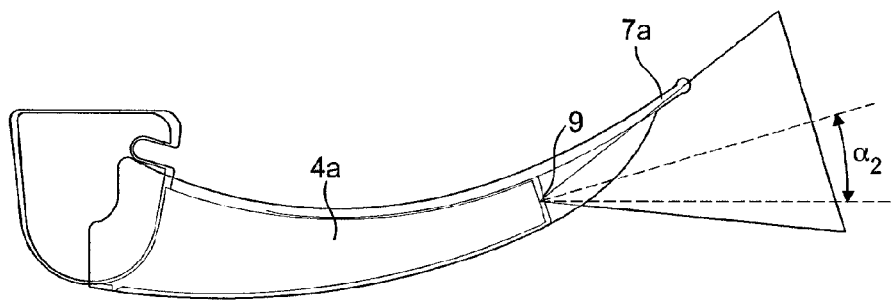
FIG. 8a shows the laryngoscope of FIG. 7 fitted with a short standard curved blade.
Figure 8B:
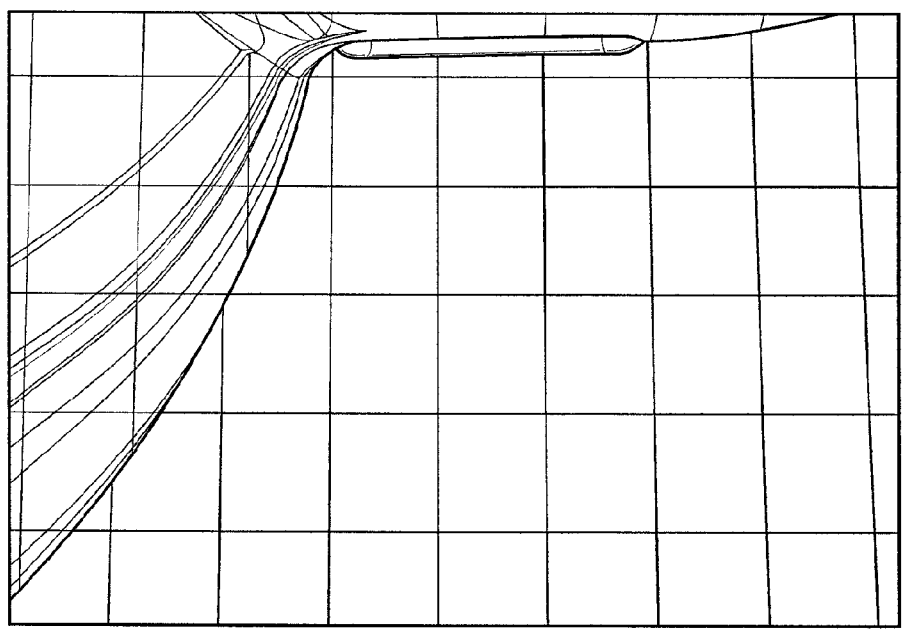
Figure 9A:
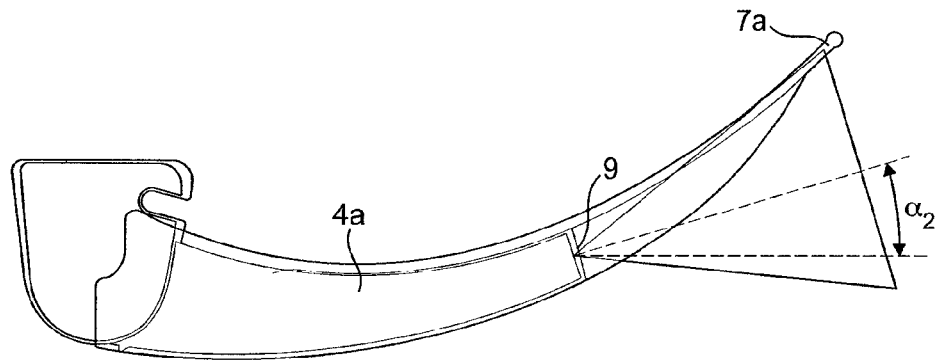
FIG. 9a shows the laryngoscope of FIG. 7 fitted with a long standard curved blade.
Figure 9B:
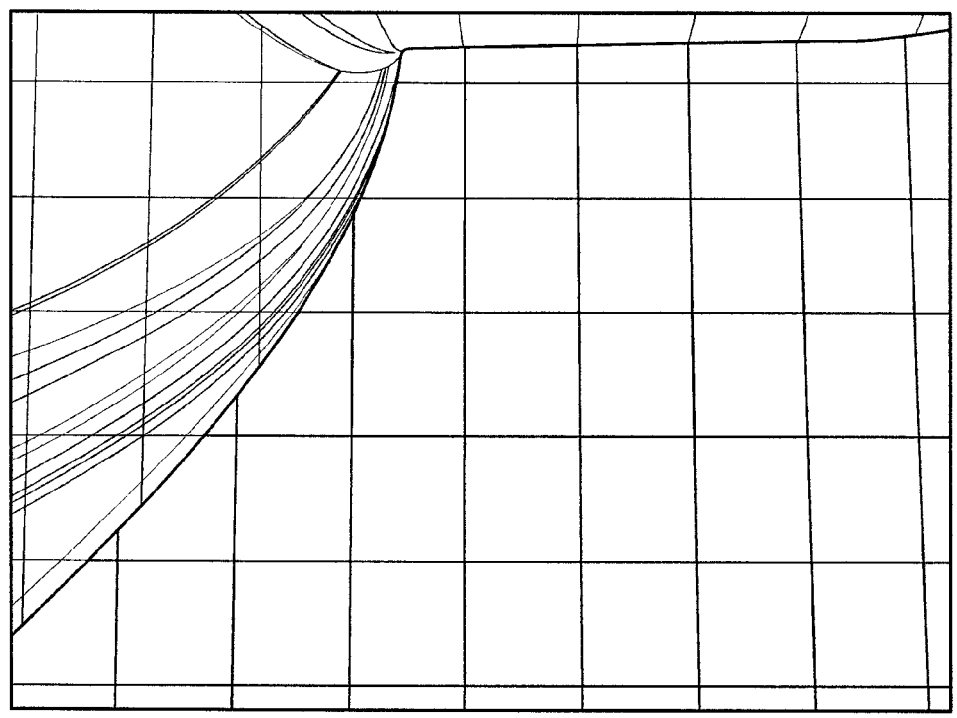

In FIGS. 8a and 9a, the blade holding element (3) is fitted with a short standard curved blade and with a long standard curved blade (4a), respectively. The views captured by the camera (9) are shown in FIGS. 8b and 9b and include the tip of the extension (7a). The views are clear and not distorted (as illustrated by the perfectly square grid). These are satisfactory views that, when positioned in the patient, precisely focus on the laryngeal inlet of the patient.

Figure 10A:
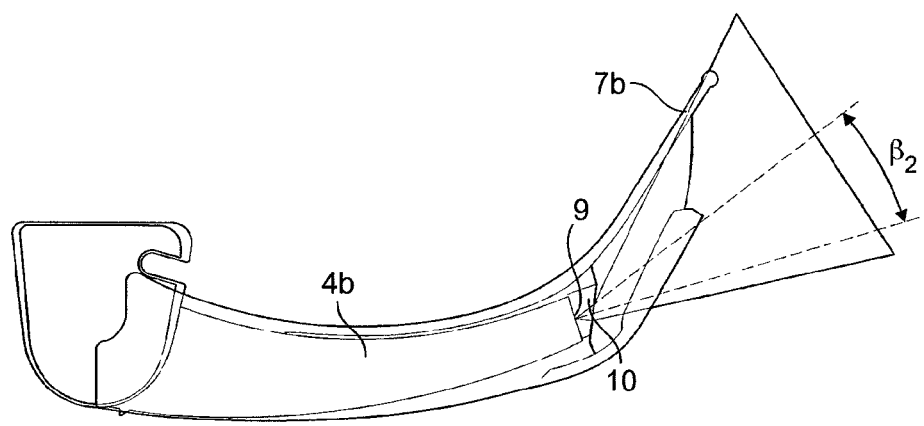
FIG. 10a shows the laryngoscope of FIG. 7 fitted with a difficult blade.
Figure 10B:
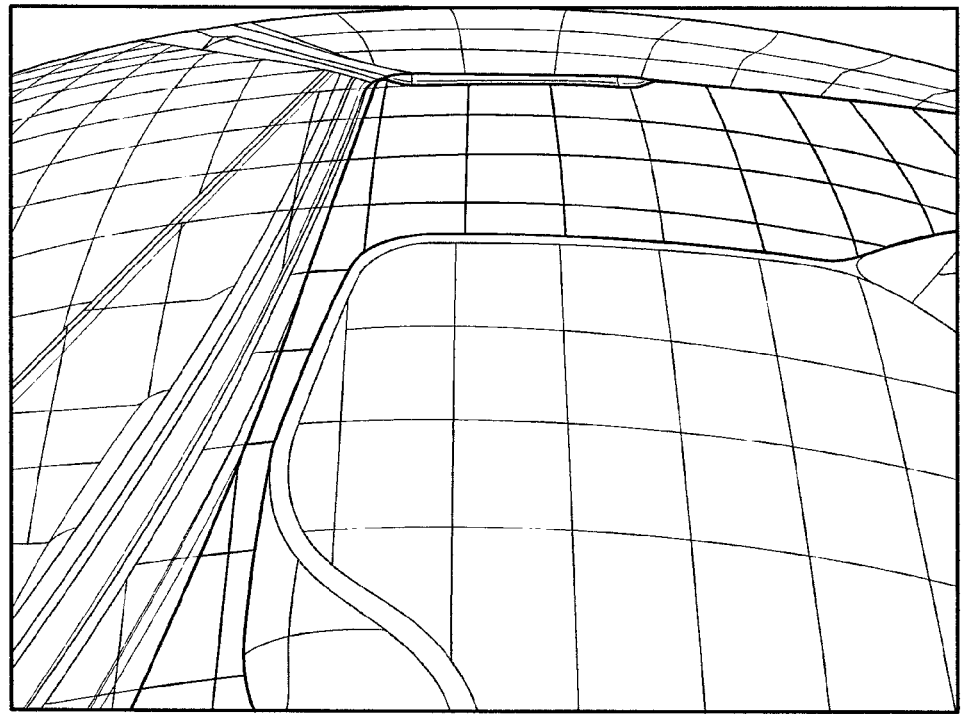

In FIG. 10a, the blade holding element (3) is fitted with a difficult blade (4b). The distal end of the sleeve (6b) comprises a wedge prism that redirects the optical pathway so that the tip of the extension (7b) is visible as shown in FIG. 10b. Preferably, the prism is chosen so that the centre of the visual field captured by the camera is located for example at an angle ranging from 30° to 45°. In FIG. 6b, the exemplary strength of the prism is 25° which provides an exemplary angle of 37° (corresponding to the original angle $\alpha_2$ of 17° plus a ventral tilt $\beta_2$ of 20°). The view captured by the camera (9) is less distorted and clearer than that obtained with the stronger wedge prism of the first embodiment (see FIG. 6b).

Embodiment 3

Figure 11:
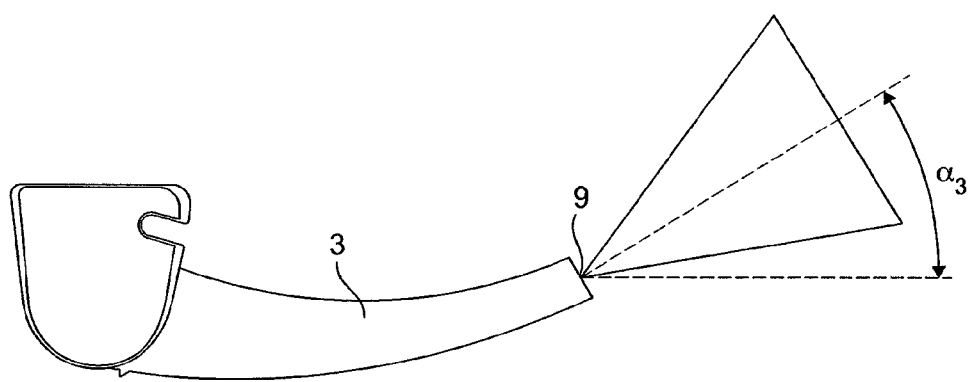
FIG. 11 shows part of a laryngoscope according to a third embodiment of the invention.

FIG. 11 shows part of a laryngoscope according to a third embodiment of the invention. The camera (9) is arranged so that the centre of the visual field captured by the camera is located at an angle $\alpha_3$ ranging for example from 25° to 40° from line H-H in the plan defined by line H-H and the longitudinal axis of the handle (2). The angle $\alpha_3$ is greater than $\alpha_1$ and $\alpha_2$ (for example 32°).

Figure 12A:
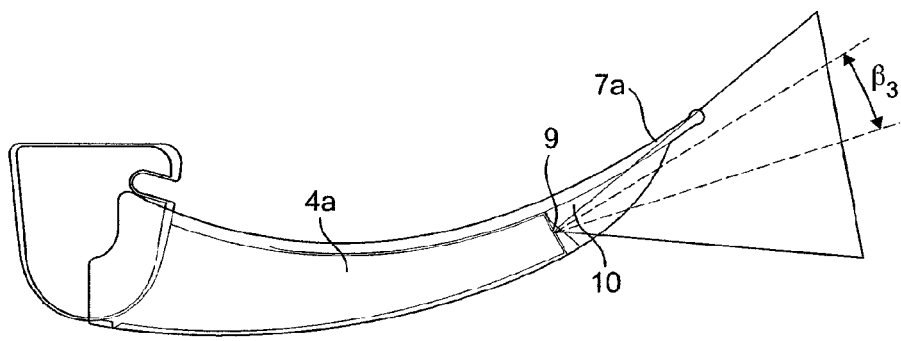
FIG. 12a shows the laryngoscope of FIG. 11 fitted with a short standard curved blade.
Figure 13A:
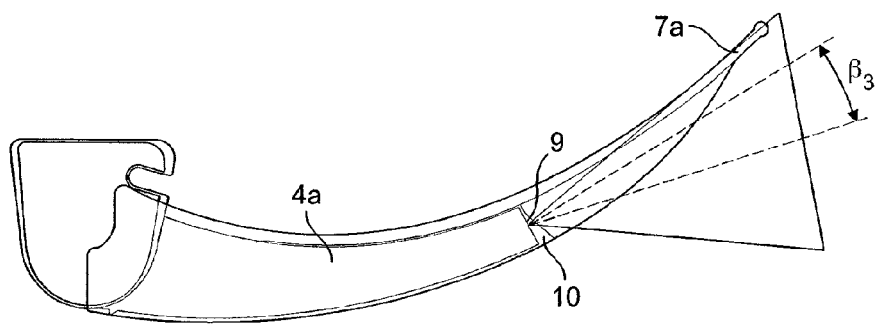
FIG. 13a shows the laryngoscope of FIG. 11 fitted with a short standard curved blade.

In FIGS. 12a and 13a, the blade holding element (3) is fitted with a short standard curved blade and with a long standard curved blade (4a), respectively. In addition, a wedge prism is fitted at the distal end of the sleeve (6a) to direct the viewing field towards the tip of the extension (7a).

Figure 12B:
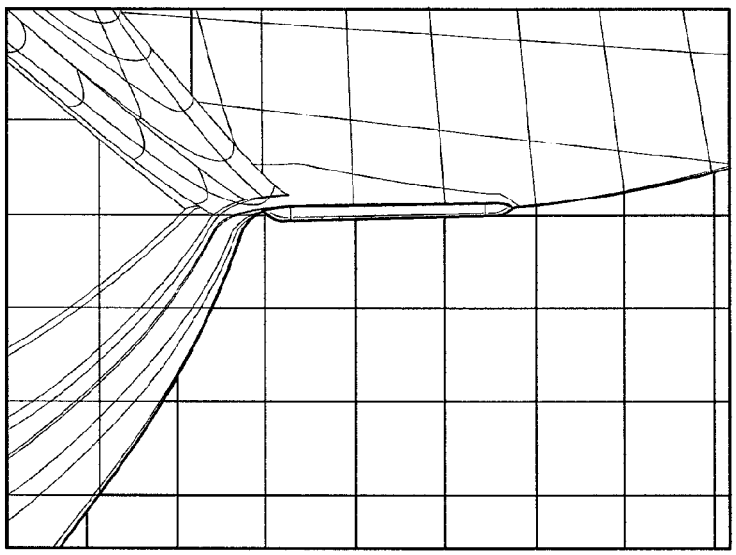
FIG. 12b shows a view obtained with the laryngoscope of FIG. 12a without a prism.
Figure 13B:
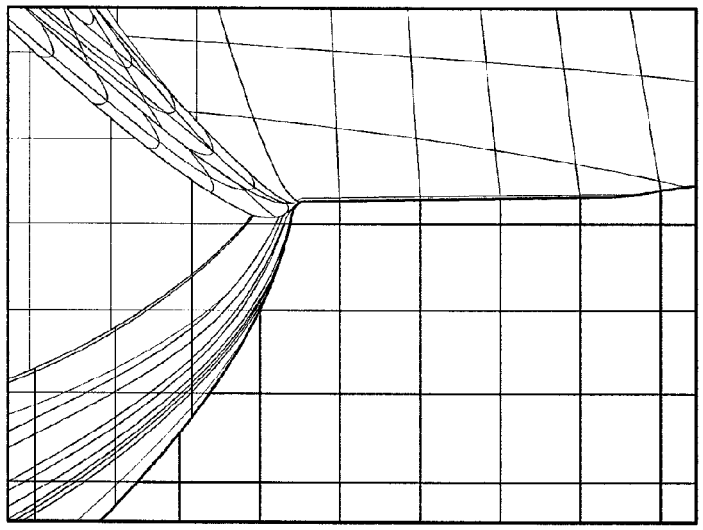
FIG. 13b shows a view obtained with the laryngoscope of FIG. 13a without a prism.

FIGS. 12b and 13b show the views obtained using the blades of FIGS. 12a and 13a and the re-positioning of the camera on its own (i.e. without a wedge prism). No distortion is observed and the view is clear. However, the extension (7a) intrudes into (approximately ⅓ of) the viewing field.

Figure 12C:
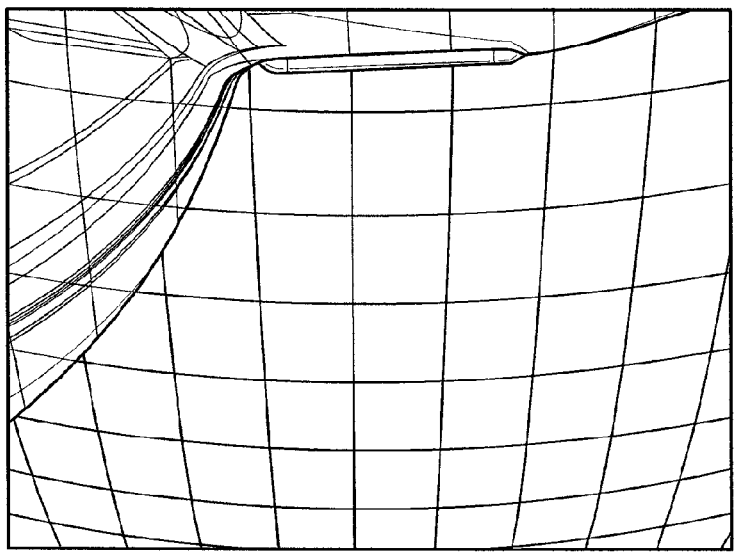
FIG. 12c shows a view obtained with the laryngoscope of FIG. 12a with a prism.
Figure 13C:
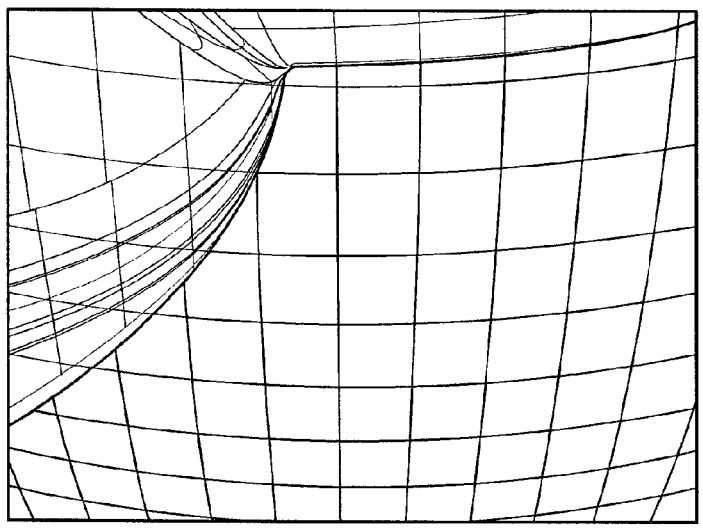
FIG. 13c shows a view obtained with the laryngoscope of FIG. 13a with a prism.

By contrast, when a wedge prism is fitted onto the blade (see FIGS. 12c and 13c), the tip of the extension is visible but does not substantially intrude into the viewing field. A slight distortion is observed but the view is sufficiently clear to allow inspection of the patient's airway to efficiently insert a tracheal tube. In FIGS. 12a and 13a, the exemplary strength of the prism is 20° which provides an exemplary angle of 18° corresponding to the original angle $\alpha_3$ of 32° minus a dorsal tilt $\beta_3$ of 14°. In this case, the tilt $\beta_3$ is subtracted from the original angle $\alpha_3$ because the wedge prism is positioned so that the view is re-adjusted dorsally and not ventrally (as in the previous embodiments).

Figure 14A:
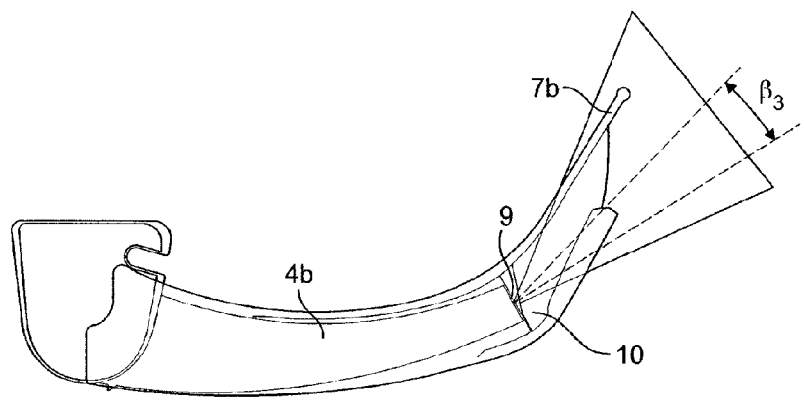
FIG. 14a shows the laryngoscope of FIG. 11 fitted with a short standard curved blade.

In FIG. 14a, the blade holding element (3) is fitted with a difficult blade (4b). The exemplary strength of the prism is 20° which provides an exemplary angle of 46° corresponding to the original angle $\alpha_3$ of 32° due to the positioning of the camera, plus a ventral tilt $\beta_3$ of 14° due to the presence of the prism. A clear view with significantly reduced distortion is obtained as can be seen in FIG. 14c.

Figure 14B:
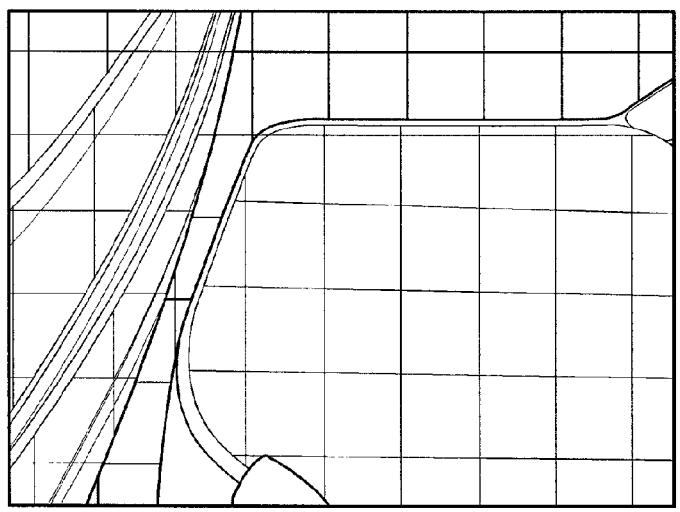
FIG. 14b shows a view obtained with the laryngoscope of FIG. 14a without a prism.
Figure 14C:
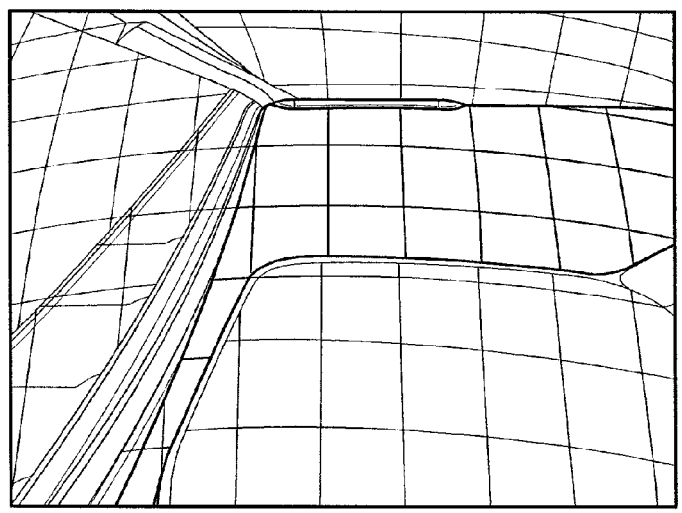
FIG. 14c shows a view obtained with the laryngoscope of FIG. 14a with a prism.

As a comparison, FIG. 14b shows a view obtained using the blade of FIG. 14a and the re-positioning of the camera on its own (i.e. without a wedge prism). No distortion is observed and the view is clear but the tip of the extension (7b) is not visible, i.e. the view is not precisely focused on the laryngeal inlet of the patient.

Embodiment 4

Figure 15:
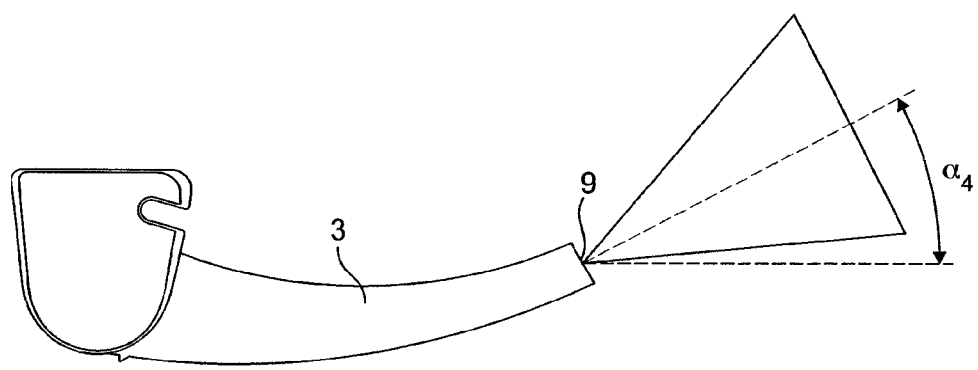
FIG. 15 shows part of a laryngoscope according to a fourth embodiment of the invention.

The laryngoscope of FIG. 15 is similar to that shown in FIG. 11. The difference is that the camera (9) is arranged so that the centre of the visual field captured by the camera is located at an angle $\alpha_4$ of for example 27.5° from line H-H in the plan defined by line H-H and the longitudinal axis of the handle (2).

Figure 16A:
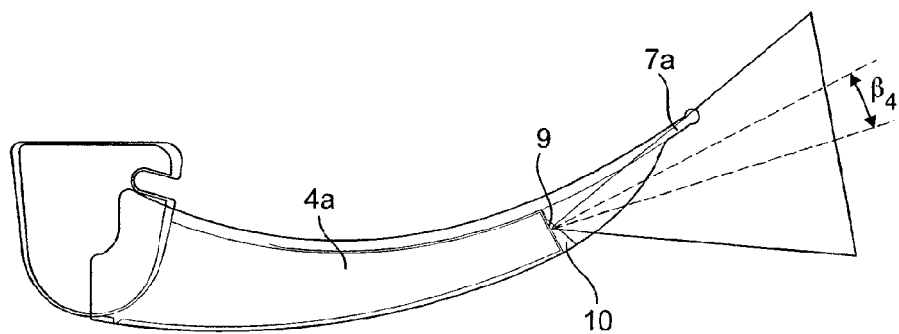
FIG. 16a shows the laryngoscope of FIG. 11 fitted with a short standard curved blade.
Figure 17A:
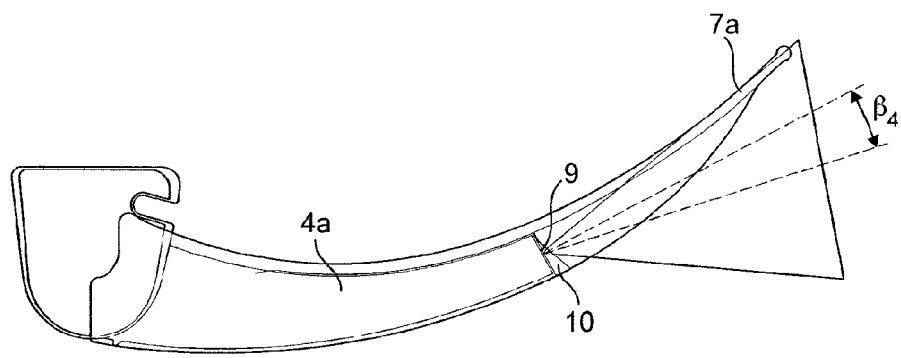
FIG. 17a shows the laryngoscope of FIG. 11 fitted with a short standard curved blade.

In FIGS. 16a and 17a, the blade holding element (3) is fitted with a short standard curved blade and with a long standard curved blade (4a), respectively. The wedge prism is weaker than that used in embodiment 3, for example with a strength of 16° and the resulting angle is 18° corresponding to the original angle $\alpha_4$ of 27.5° due to the positioning of the camera, minus a dorsal tilt $\beta_4$ of 9.5° due to the presence of the prism.

Figure 16B:
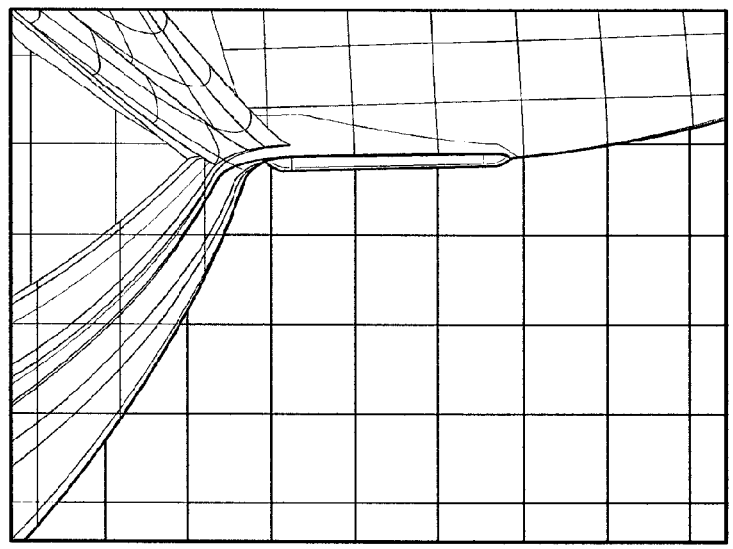
FIG. 16b shows a view obtained with the laryngoscope of FIG. 16a without a prism.
Figure 16C:
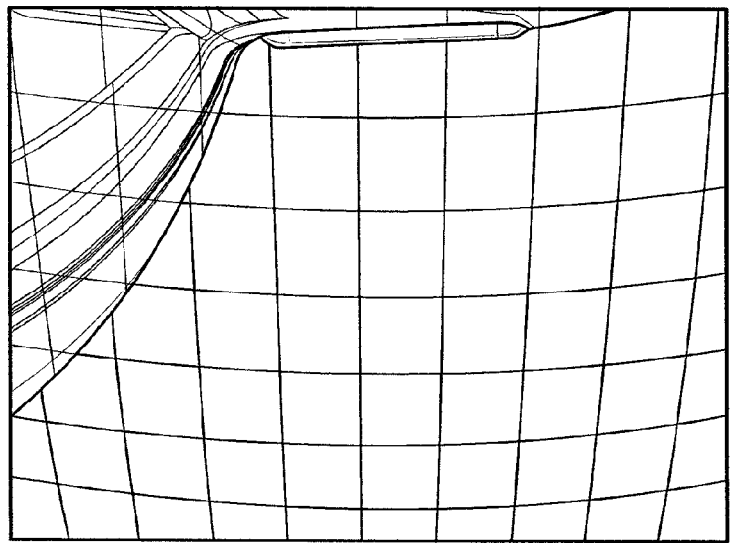
FIG. 16c shows a view obtained with the laryngoscope of FIG. 16a with a prism.
Figure 17B:
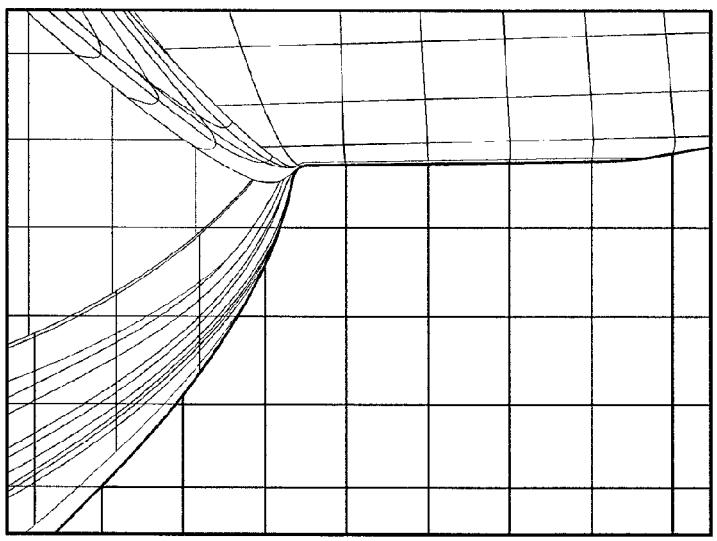
FIG. 17b shows a view obtained with the laryngoscope of FIG. 17a without a prism.
Figure 17C:
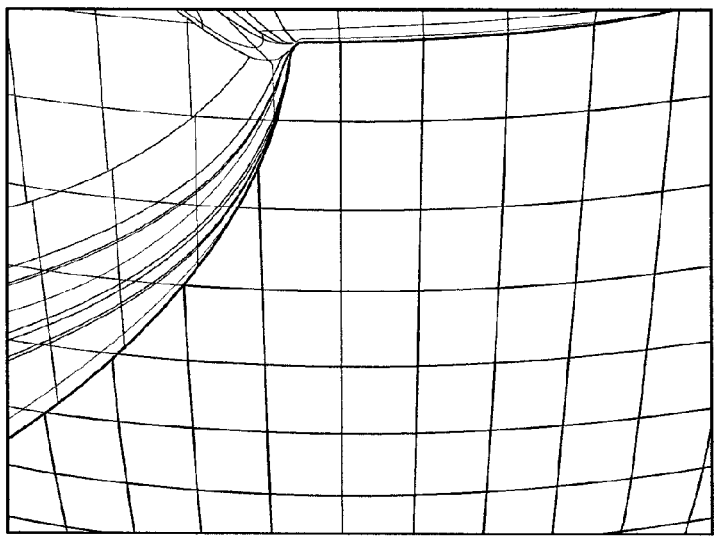
FIG. 17c shows a view obtained with the laryngoscope of FIG. 17a with a prism.

As can be seen on FIGS. 16b and 17b, the extension (7a) intrudes into the viewing field when the blade (4a) is not fitted with a wedge prism, but the view is clear and non-distorted. When the prism is fitted to the distal end of the sleeve (5a) of the blade (4a), then only the tip of the extension (7a) is visible, thereby indicating that a focused view of the laryngeal inlet can be obtained (see FIGS. 16c and 17c). There is little distortion and the view is clear.

Figure 18A:
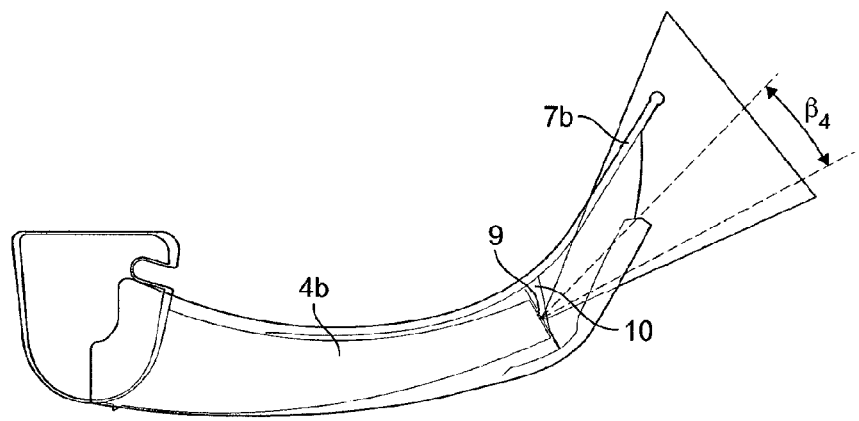
FIG. 18a shows the laryngoscope of FIG. 11 fitted with a short standard curved blade.

In FIG. 18a, the blade holding element (3) is fitted with a difficult blade (4b). The exemplary strength of the prism is 21.5° which provides an exemplary angle of 45° corresponding to the original angle $\alpha_4$ of 27.5° due to the positioning of the camera, plus a ventral tilt $\beta_4$ of 17.5° due to the presence of the prism. A clear view with significantly reduced distortion is obtained as can be seen in FIG. 18c.

Figure 18B:
FIG. 18b shows a view obtained with the laryngoscope of FIG. 18a without a prism.
Figure 18C:
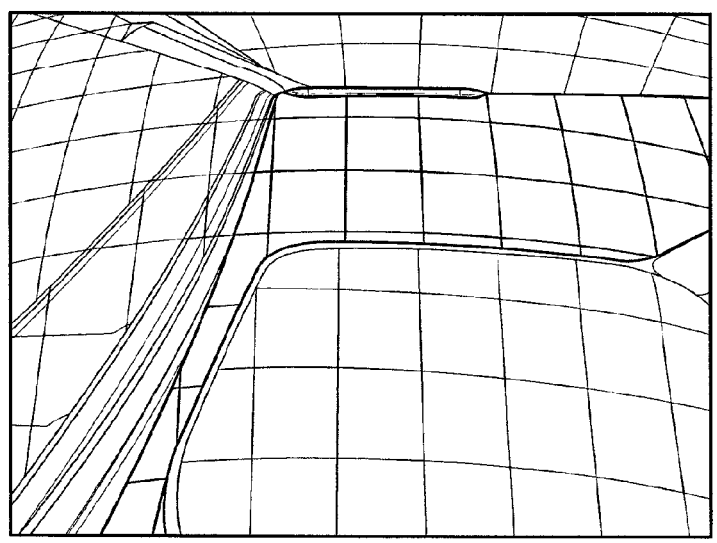
FIG. 18c shows a view obtained with the laryngoscope of FIG. 18a with a prism.
Figure 19:
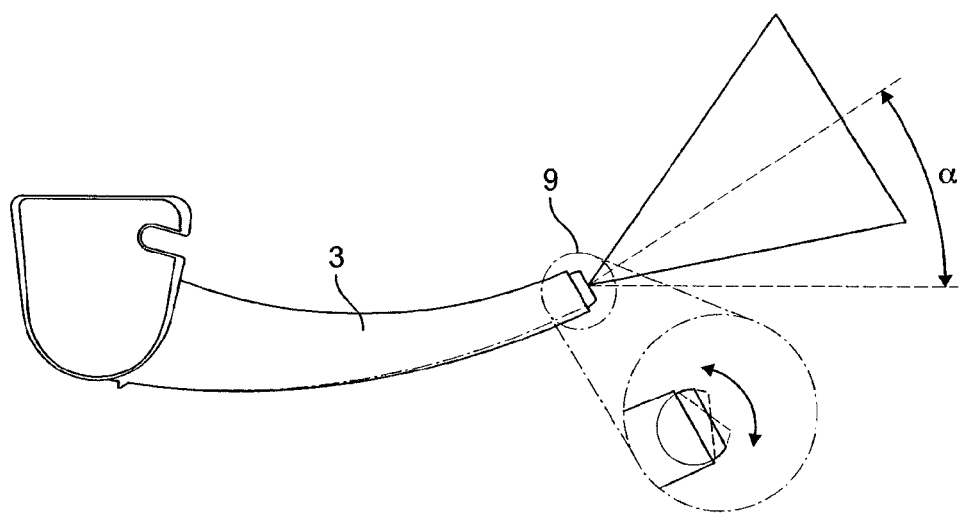
FIG. 19 shows part of a laryngoscope according to a second embodiment of the invention.

As a comparison, FIG. 18b shows a view obtained using the blade of FIG. 18a and the re-positioning of the camera on its own (i.e. without a wedge prism). No distortion is observed and the view is clear but the tip of the extension (7b) is not visible.

Embodiment 5

The distal end of the blade holding element (3) may be fitted with at least a first and a second camera (9). The first camera may be positioned so that a clear, non-distorted view of the laryngeal inlet is obtained when using a standard blade and the second camera may be positioned so that a clear, non-distorted view of the laryngeal inlet is obtained when using a difficult blade. A laryngoscope fitted with such a viewing means enables the clinician to use one laryngoscope for at least standard and difficult blades, thereby limiting expenses. In addition, this type of laryngoscope may be used with blades which do not require a prism or any other means of adjusting the viewing field, since the viewing field is already adjusted using a multi-camera system.

The laryngoscope (1) may further comprise means (for example electronic means) for switching from one camera to the other so that the clinician may select to use the first and/or the second camera depending on the view required and the type of blade fitted onto the blade holding element.

Embodiment 6

The inventors further developed the laryngoscope of Embodiment 5 by replacing the multi-camera system with a single movable or "tiltable" camera (9) fitted at the distal end of the blade holding element (3). For example, the camera may be encased in a low friction housing, it may be fitted with a mechanical or electronic means of tilting the camera so that the viewing field is focused on the laryngeal inlet of the patient. This type of laryngoscope may be used with blades which do not require any prism or any other means of adjusting the viewing field.

Figure 20A:
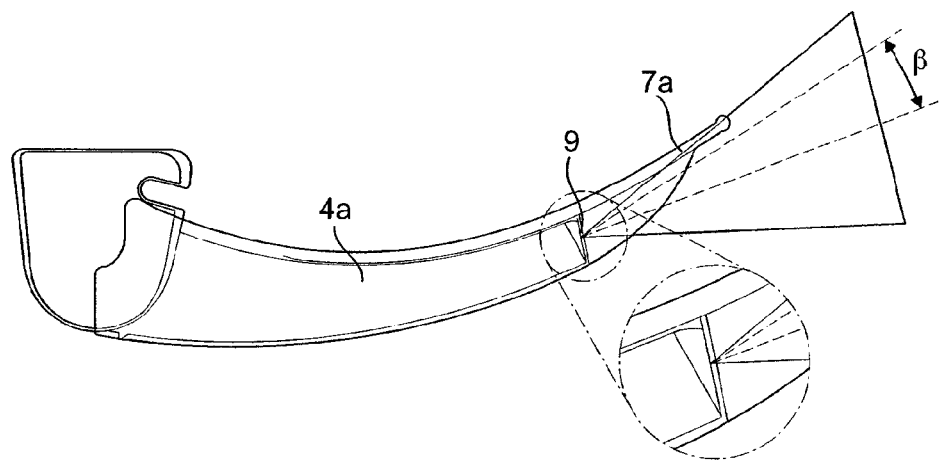
FIG. 20a shows the laryngoscope of FIG. 9 fitted with a short standard curved blade.
Figure 20B:
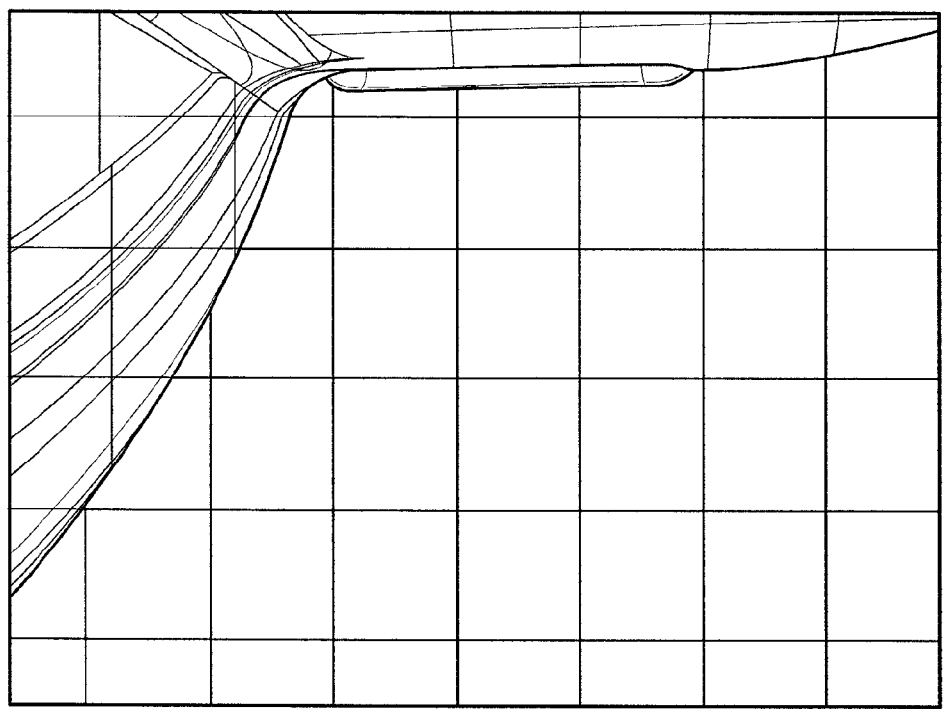
Figure 21A:
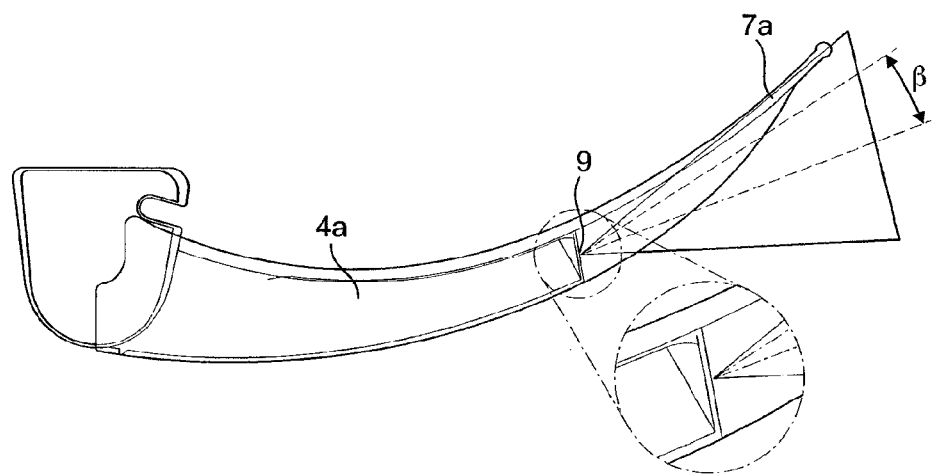
FIG. 21a shows the laryngoscope of FIG. 9 fitted with a long standard curved blade.
Figure 21B:
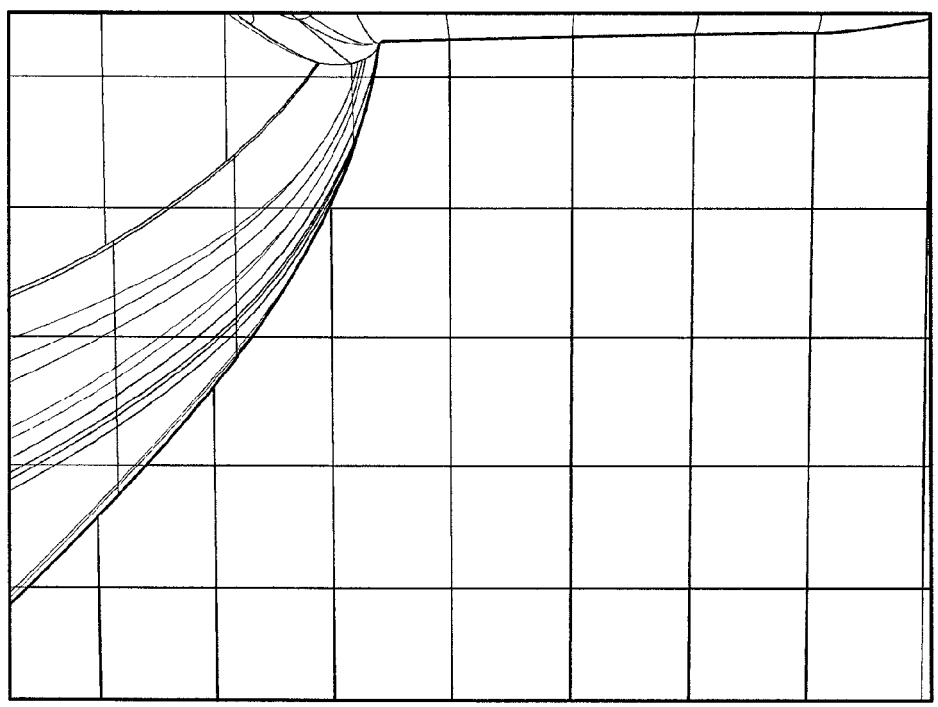
Figure 22A:
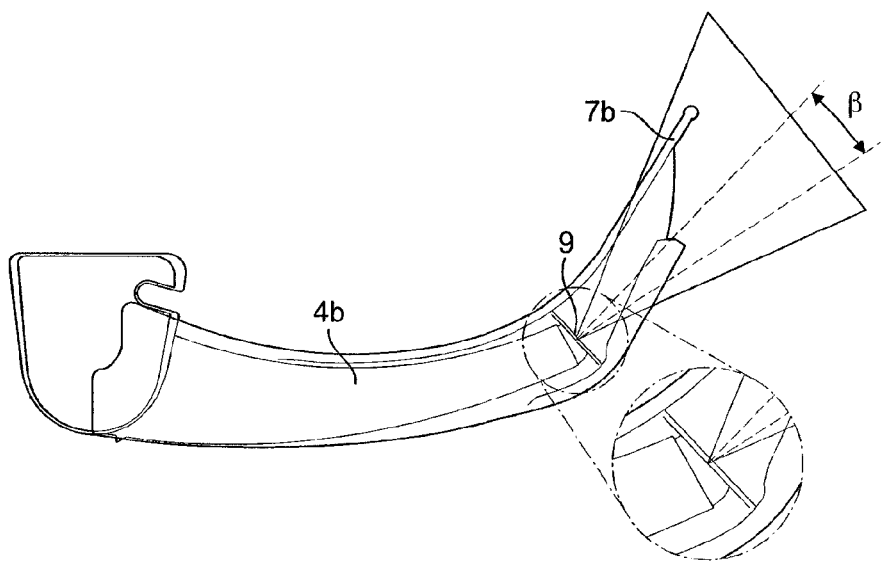
FIG. 22a shows the laryngoscope of FIG. 9 fitted with a difficult blade.
Figure 22B:
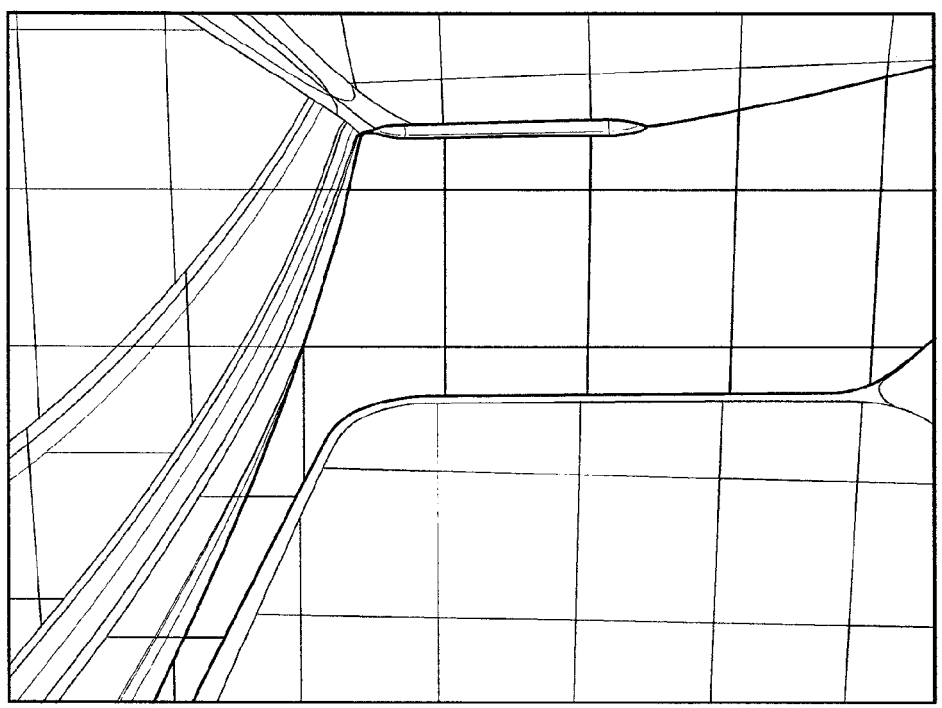

The laryngoscope (1) may further comprise means for positioning the camera in the desired position so that a clear, non-distorted view of the laryngeal inlet. For example, the laryngoscope may comprise mechanical or electronic means for remotely changing the position of the camera. Alternatively, the blades may be such that the position of the camera is automatically adjusted when the blade is fitted onto the blade holding element. For example, the distal end (6) of the sleeve (5) may be built or moulded at an angle so that upon fitting the blade onto the blade holding element, the distal end or window (6) pushes the camera into a position suitable for viewing the tip of the extension (7) of the blade in a clear and non-distorted manner. Such constructions are shown in FIGS. 20a, 21a and 22a and the corresponding views are shown in FIGS. 20b, 21b and 22b.

Where the blade comprises a wedge prism, the prism may be fitted onto the blade by any suitable means, including for example screws and/or glue. Preferably, the prism is integrally moulded at the distal end of the sleeve. An integrally mounted prism has the advantage of being less expensive, more robust and less prone to contamination.

It is believed that currently more than 95% of all intubations can be carried out using a standard blade, which means that clinicians need to buy a laryngoscope, specifically designed for use with a difficult blade, for the remaining 5% (or less) of the intubations. The laryngoscope described above enables clinicians to minimise expenses because only one universal laryngoscope is required for use with physically and functionally dissimilar blades. In addition, the different types of blade may be used interchangeably without substantially compromising the clarity of the view of the patient's laryngeal inlet.

The invention claimed is:

1. A laryngoscope comprising:
   a handle,
   an elongate blade holding element pivotally attached to the handle, the elongate blade holding element comprising means for viewing the laryngeal inlet of a patient, and
   at least two different detachable blades, at least one of the two different detachable blades comprising means for adjusting a viewing field of the means for viewing the laryngeal inlet of a patient such that a tip of a distal extension in the at least one of the two different detachable blades is visible to the means for viewing the laryngeal inlet of a patient.

2. The laryngoscope according to claim 1, wherein each of the at least two different detachable blades comprises a hollow sleeve portion and the distal extension.

3. The laryngoscope according to claim 2, wherein each of the at least two different detachable blades further comprises means for guiding an endotracheal tube towards a tip of the distal extension.

4. The laryngoscope according to claim 1, wherein the means for viewing comprises at least one fixed camera located at a distal end of the blade holding element.

5. The laryngoscope according to claim 1, wherein the means for adjusting the viewing field comprises a prism or a wedge prism.

6. The laryngoscope according to claim 1, wherein the means for viewing comprises at least two fixed cameras directed to at least two different viewing fields.

7. The laryngoscope according to claim 6, further comprising means for switching from one of the at least two fixed cameras to the other.

8. The laryngoscope according to claim 1, wherein the means for viewing comprises a movable camera.

9. The laryngoscope according to claim 8, further comprising mechanical or electronic means for controlling the movement of the camera.

10. The laryngoscope according to claim 8, wherein a distal end of a sleeve portion of the at least two different detachable blades comprises a window positioned such that, in use, the camera is positioned to visualise the laryngeal inlet of the patient.

11. A method for viewing the laryngeal inlet of a patient using the laryngoscope of claim 1, the method comprising assessing a patient, determining if the patient has anatomical abnormalities or injuries that require use of a detachable blade comprising means for adjusting a viewing field of a means for viewing the laryngeal inlet of the patient such that a tip of a distal extension of the blade is visible to the means for viewing the laryngeal inlet of the patient, then if required, fitting the detachable blade comprising means for adjusting a viewing field of a means for viewing the laryngeal inlet of the patient such that a tip of a distal extension is visible to the means for viewing the laryngeal inlet of the patient onto the blade holding element in order to achieve the required viewing angle.

12. The method of claim 11, wherein the means for viewing comprises at least one camera element and the detachable blade comprises a light refracting means capable of redirecting the optical pathway of the camera element.

13. The method of claim 11, wherein the means for viewing comprises at least two camera elements and the viewing field is adjusted by switching the view from one of the camera elements to the other.

14. The method of claim 11, wherein the means for viewing comprises at least one camera element and the viewing field is adjusted by moving the camera element.

15. A laryngoscope comprising:
    a handle,
    a blade holding element pivotally attached to the handle, the blade holding element having a camera located at a distal end of the blade holding element for viewing the laryngeal inlet of a patient,
    a detachable blade slidable relative to and fitted onto the blade holding element,
    the detachable blade comprising a means for adjusting a viewing field of the camera forming an integrally moulded part of the detachable blade such that a tip of the detachable blade is visible to the camera.

16. The laryngoscope according to claim 15, wherein the detachable blade comprises a hollow sleeve portion and a distal extension.

17. The laryngoscope according to claim 16, wherein a distal end of the sleeve portion of the detachable blade comprises a window positioned proximate the distal end of the blade holding element, the window comprising the means for adjusting a viewing field of the camera, the means for adjusting a viewing field of the camera comprising a light refracting means.

18. The laryngoscope according to claim 17, wherein the light refracting means is a prism or a wedge prism.

19. A laryngoscope comprising:
    a handle,
    an elongate blade holding element pivotally attached to the handle, the elongate blade holding element comprising means for viewing the laryngeal inlet of a patient, and
    at least two different detachable blades slidable relative to the blade holding element, at least one of the two different blades comprising an integrally moulded means for adjusting a field of view of the means for viewing the laryngeal inlet of a patient such that a tip of at least one of the two different detachable blades is visible to the means for viewing the laryngeal inlet of a patient.

20. The laryngoscope according to claim 1, wherein the at least one of the two different detachable blades comprising means for adjusting the viewing field of the means for viewing the laryngeal inlet of a patient further comprises a distal extension.

21. The laryngoscope according to claim 20, wherein the viewing field covers at least a 30° viewing angle below a tip of the distal extension.

22. A kit comprising the laryngoscope according to claim 1 and a detachable display screen.

23. The laryngoscope according to claim 2, wherein the hollow sleeve portion of each of the at least two different detachable blades comprises an inner contour that corresponds substantially to an outer contour of the elongate blade holding element.

24. The laryngoscope according to claim 1, wherein the means for viewing is positioned in the blade holding element such that a center of the viewing field captured by the means for viewing is located at an angle between 5° and 40° below a line that passes between a center of the means for viewing and a pivotal joint between the handle and the blade holding element.

25. The laryngoscope according to claim 24, wherein the means for adjusting the viewing field is adapted to adjust the viewing field of the means for viewing to have at least a 30° viewing angle below a tip of a distal extension of the at least two different detachable blades.

26. A laryngoscope comprising:
   a handle,
   an elongate blade holding element attached to the handle, the elongate blade holding element comprising means for viewing the laryngeal inlet of a patient, and
   at least two different detachable blades, at least one of the two different detachable blades comprising means for adjusting a viewing field of the means for viewing the laryngeal inlet of a patient such that a tip of a distal extension in the at least one of the two different detachable blades is visible to the means for viewing the laryngeal inlet of a patient.

27. The laryngoscope according to claim 26, wherein each of the at least two different detachable blades comprises a hollow sleeve portion and the distal extension.

28. The laryngoscope according to claim 27, wherein each of the at least two different detachable blades further comprises means for guiding an endotracheal tube towards a tip of the distal extension.

29. The laryngoscope according to claim 26, wherein the means for viewing comprises at least one fixed camera located at a distal end of the blade holding element.

30. The laryngoscope according to claim 26, wherein the means for adjusting the viewing field comprises a prism or a wedge prism.

31. The laryngoscope according to claim 26, wherein the means for viewing comprises at least two fixed cameras directed to at least two different viewing fields.

32. The laryngoscope according to claim 31, further comprising means for switching from one of the at least two fixed cameras to the other.

33. The laryngoscope according to claim 26, wherein the means for viewing comprises a movable camera.

34. The laryngoscope according to claim 33, further comprising mechanical or electronic means for controlling the movement of the camera.

35. The laryngoscope according to claim 33, wherein a distal end of a sleeve portion of the at least two different detachable blades comprises a window positioned such that, in use, the camera is positioned to visualise the laryngeal inlet of the patient.

* * * * *